(12) United States Patent
Carrington

(10) Patent No.: US 7,098,469 B1
(45) Date of Patent: Aug. 29, 2006

(54) FORENSIC LIGHT SOURCE KIT

(76) Inventor: John Carrington, 100 Hunter Pl., Youngsville, NC (US) 27596

( * ) Notice: Subject to any disclaimer, the term of this patent is extended or adjusted under 35 U.S.C. 154(b) by 56 days.

(21) Appl. No.: 10/786,508

(22) Filed: Feb. 25, 2004

(51) Int. Cl.
G02B 1/00 (2006.01)
(52) U.S. Cl. .................................. 250/504 H; 356/418
(58) Field of Classification Search ................ 250/504, 250/504 H
See application file for complete search history.

(56) References Cited

U.S. PATENT DOCUMENTS 4,933,816 A * 6/1990 Hug et al. .................. 362/551
6,862,093 B1 * 3/2005 Peng et al. ................. 356/418
6,954,270 B1 * 10/2005 Ostler et al. ................ 356/318
2005/0111233 A1 * 5/2005 Vezard et al. ............... 362/552

FOREIGN PATENT DOCUMENTS

GB 2389412 A * 12/2003

* cited by examiner

Primary Examiner—Nikita Wells
Assistant Examiner—Phillip A. Johnston
(74) Attorney, Agent, or Firm—Mills Law Firm PLLC

(57) ABSTRACT

A forensic light source kit including a portable light source having a self contained battery and a white light source with a plurality of sliding filters for providing selected wavelength illumination, a plurality of barrier filter goggles, a tripod for mounting the light source, and a carrying case therefor.

9 Claims, 10 Drawing Sheets

FORENSIC LIGHT SOURCE KIT

FIELD OF THE INVENTION

The present invention relates to forensic investigation, and, in particular, to a light source kit for detecting and recording items of forensic interest, such as physiological fluids, fluorescent chemicals and powders, and microparticle evidence.

BACKGROUND OF THE INVENTION

The systematic identification and securing of trace evidence at a crime scene is of crucial importance in crime investigation. Each scene may present a myriad of forensic residues, not readily visible to the naked eye. Fibers, fluorescent powders, body fluids, blood traces, semen, stained prints and other forensic residues are best observed and recorded when illuminated at certain wavelengths. Accordingly, light source and filtration packages have been available to permit the user to investigate for such forensic residues. The light sources have been typically externally powered, using shoulder mounted battery packs or electrical cables. The electrical cables limit the ease with which the user can scan a scene particularly in narrow or small areas.

SUMMARY OF THE INVENTION

The present invention provides a compact, self-contained light source that is fully portable about an investigation scene without connecting cables or shoulder packs allowing the investigator unlimited freedom in movement thereby simplifying the location of items of forensic interest. The instrument may be hand-held in two different positions or mounted on a standard photographic tripod. The portability and freedom of movement permits searching a multitude of surfaces in compact situations.

A xenon arc lamp provides a high intensity white light illumination approaching sunlight for locating hairs, fibers, dust prints and other like evidence. Filters covering a spectrum of about 365 nm to 650 nm may be individually selected for detecting and identifying many forms of physical evidence such as semen, saliva, materials with natural fluorescence, and items treated with fluorescent powders and dyes. The filters are carried on slide that may be inserted into the light source for quick selection of discrete wavelengths and for ready changeover from one slide to another.

The light source is incorporated in a kit carrying ancillary components for a single package, full investigation of evidence, without the need for separate accessory equipment. In addition to the light source and filter slides, a set of goggles are provided for operator safety under the various illumination conditions and for enhancing the observability of detected evidence. A tripod is provided for supporting the light source to provide the selected illumination during photographic record. Three camera lens barrier filters are provided for blocking of the source excitation light while recording to photographic media. Plural rechargeable battery packs and a battery recharger are included to permit extended operation at the scene or laboratory. The light source kit thus provides a complete kit of all equipment needed for an intense, thorough search for evidence at a crime scene or in the laboratory.

Accordingly, it is an object of the invention to provide a forensic light source providing selective wavelength illumination of a scene for detecting forensic evidence.

Another object of the invention is to provide a forensic light source kit for detecting and identifying forensic evidence observable under varying wavelength illumination.

A further object of the invention is to provide a lamp assembly for locating forensic evidence that may be deployed by a single person for scanning and discretely identifying varying forms of evidentiary residues observable only under a plurality of wavelength illuminations.

DESCRIPTION OF THE DRAWINGS

The above and other objects and advantages of the present invention will become apparent upon reading the following detailed description taken in conjunction with the accompanying drawings in which.

DETAILED DESCRIPTION OF THE PREFERRED EMBODIMENTS

Figure 1:
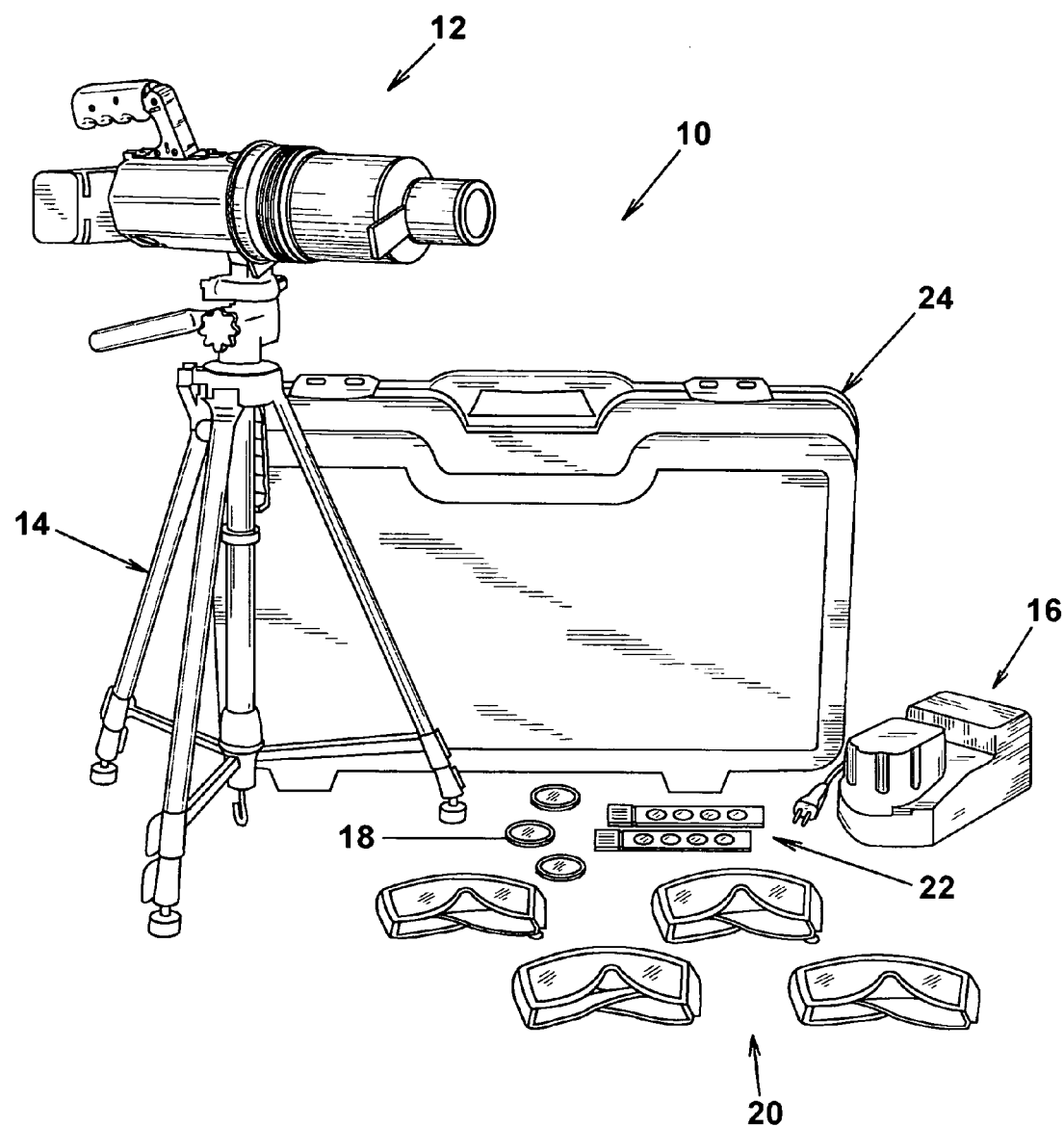
FIG. 1 is a perspective view of a forensic light source kit in accordance with a preferred embodiment of the invention.

Referring to the drawings, FIG. 1 illustrates a forensic light source kit 10 for the detection of trace forensic residues at an investigation site, such as a crime scene or laboratory. The light source kit 10 includes a forensic light source 12 detachably mounted on a tripod 14, a rechargeable battery pack assembly 16, three camera lens barrier filters 18, a set of barrier filter goggles 20, and a pair of filter slides 22, all of which are nested and transported for use in a carrying case 24. The light source 12 is lightweight, compact and self-contained, providing portability about an investigation site, without interconnecting electrical cables or body carried power supplies, thereby enabling the ready scanning of the site for detecting residuals of forensic evidence. The light source permits efficient searching of a multitude of surfaces, even when working in tight situations. The light source is particularly effective when searching for microparticle, physiological or latent print evidence. The light source may be hand held in two different positions with a detachable carrying handle, and fixedly mounted on a standard photographic tripod for recording detected residues with conventional photographic techniques.

Using a high powered xenon arc lamp a white light beam is projected, and the filter slides may be selectively deployed by a simple detented sliding movement to cover a wide spectrum of wavelengths needed to identify varying forms of physical evidence such as semen, saliva, materials with natural fluorescence, and fluorescent powders and dyes. The unfiltered high intensity white light is effective for locating hairs, dust prints, and fibers.

Figure 9:
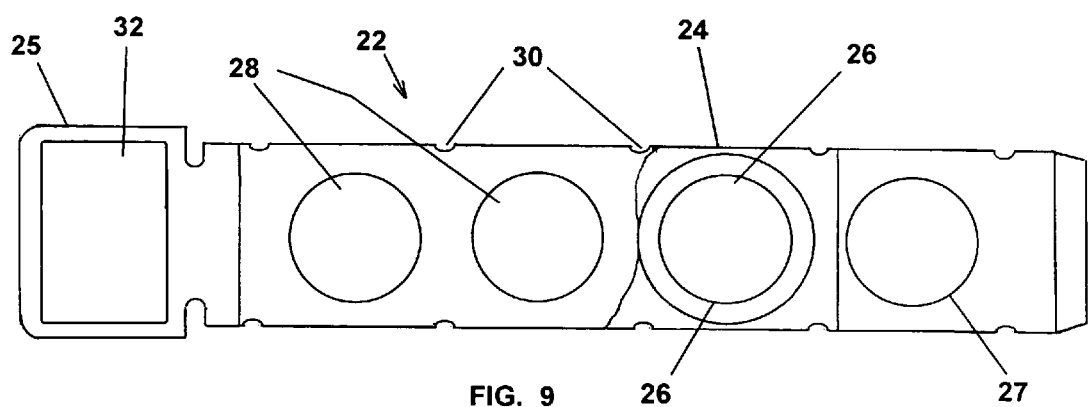
FIG. 9 is a front view of the filter array for the forensic light source.
Figure 10:
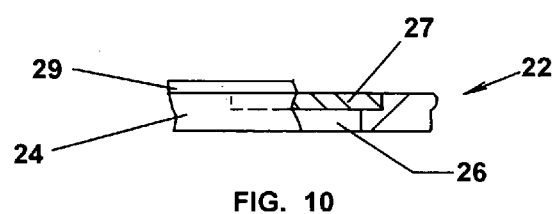
FIG. 10 is a fragmentary side sectional view illustrating the mounting of the filter on the filter array.

Referring to FIGS. 9 and 10, each filter slide 22 comprises a generally rectangular slide body 24 having an enlarged actuator tab 25, preferably formed of aluminum bar stock and anodized. The slide body 24 has a longitudinal series of circular holes. The three inner holes 26 include a counterbore. The outer hole 27 is a through hole. Wavelength filters 28 are located in the counterbores and retained therein by a cover plate 29. The individual filters provide differing projected wavelengths as described in greater detail below. The outer hole 27 permits unobstructed, unfiltered illumination. The top and bottom walls of the slide body 24 are provided with detent notches 30 for permitting the filters to be discretely located at selected transverse positions. The actuator tab 25 includes a recessed pocket for adhering a label 32 indicating the wavelengths and location of the various filters.

Figure 2:
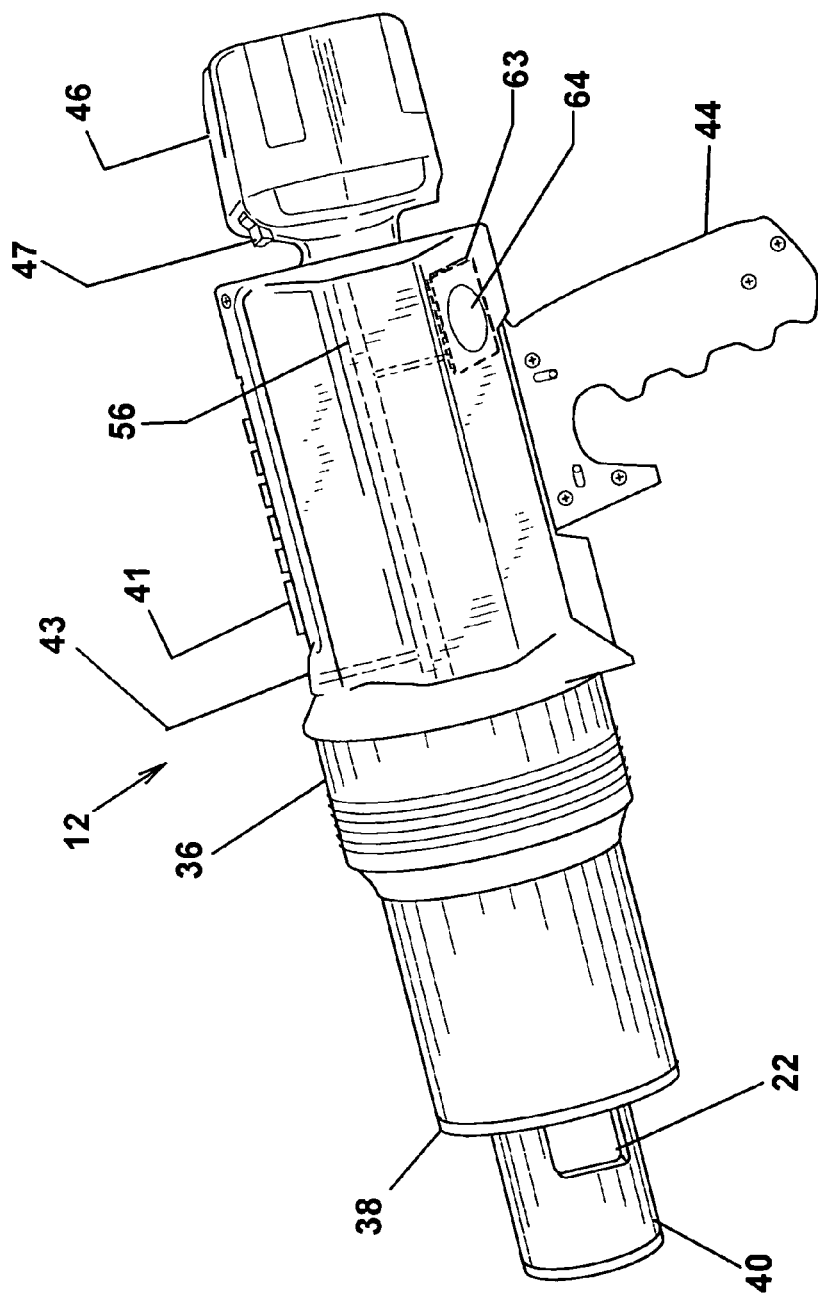
FIG. 2 is a side perspective view of the forensic light source with the carrying handle in the bottom position.
Figure 3:
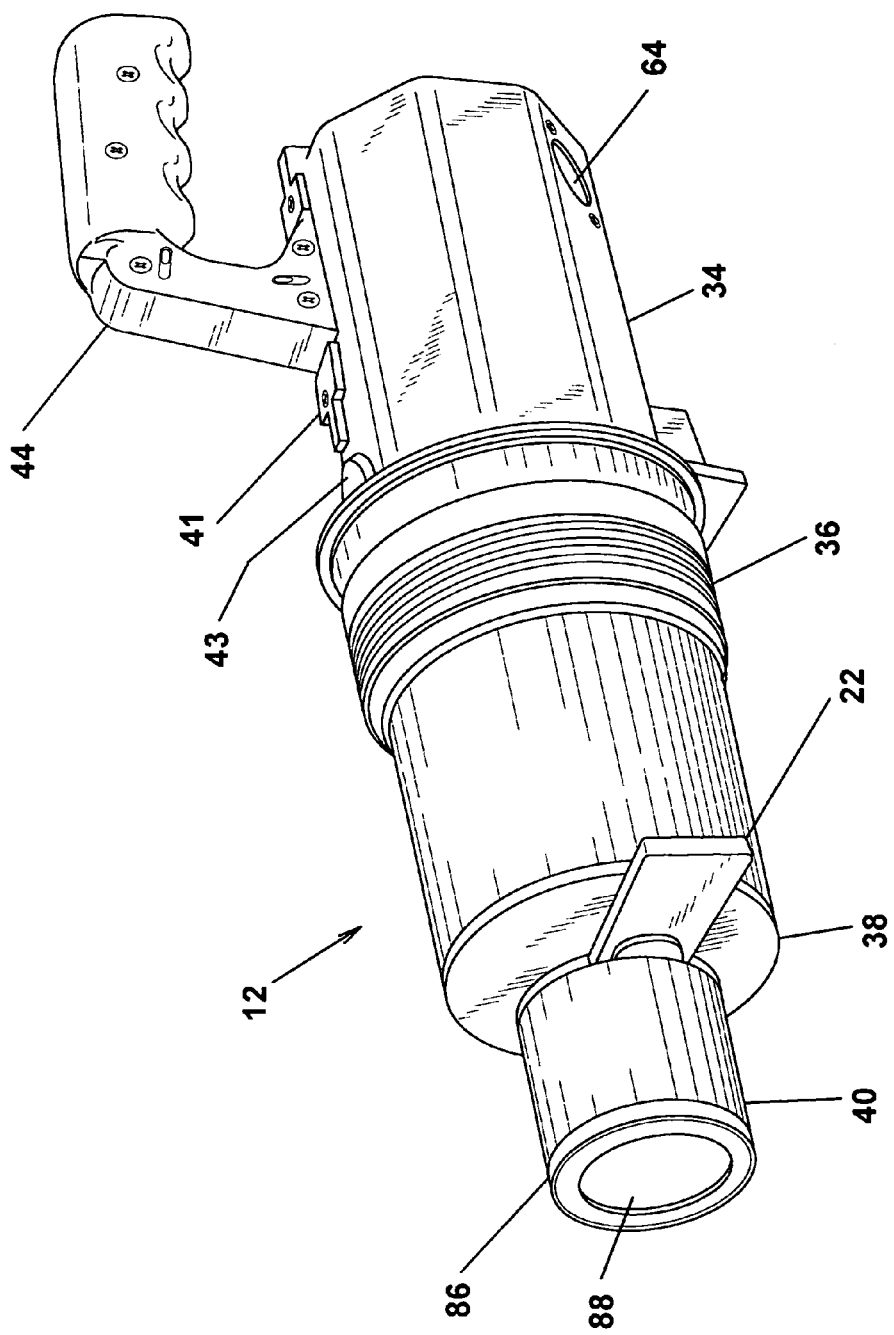
FIG. 3 is a side perspective view of the forensic light source with the carrying handle in the top position.
Figure 4:
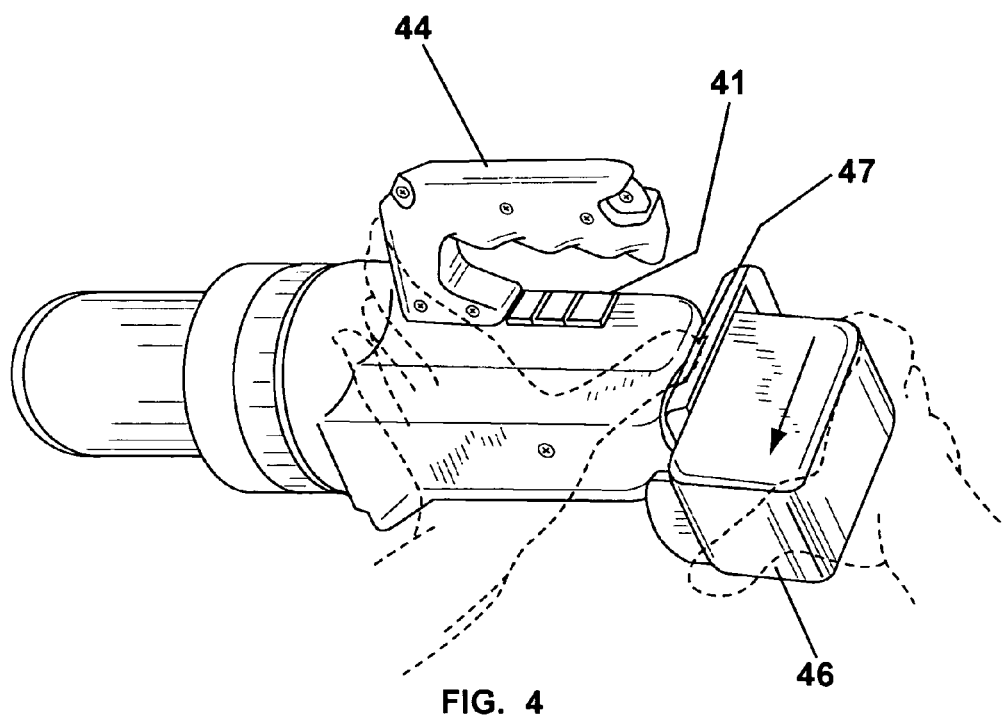
FIG. 4 is a side perspective view illustrating removal of the battery pack from the forensic light source.
Figure 5:
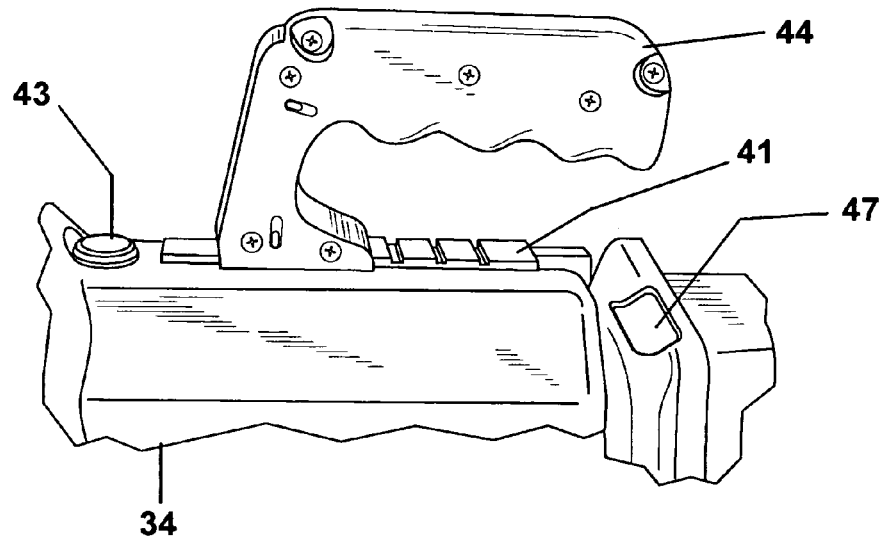
FIG. 5 is a partial perspective view illustrating the mounting of the carrying handle on the adjustable locking bracket.
Figure 6:
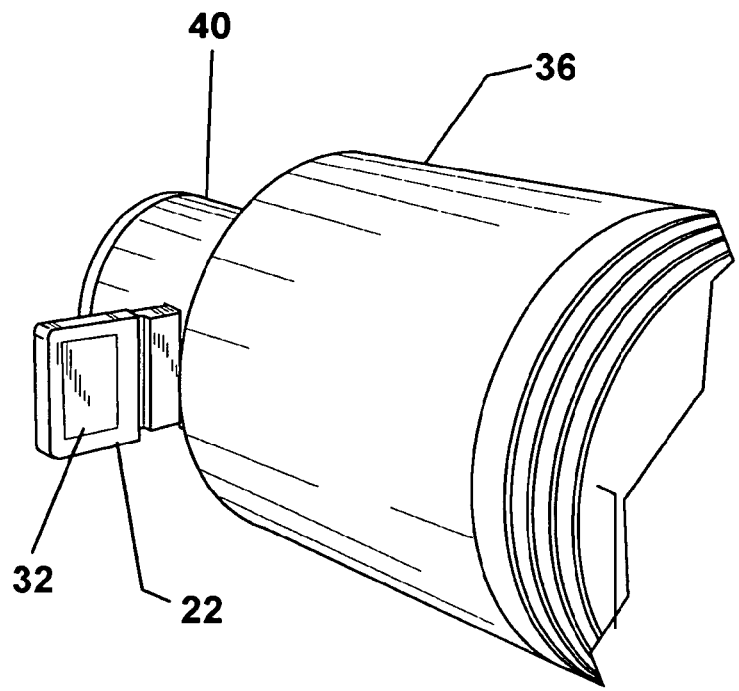
FIG. 6 is a partial perspective view illustrating the mounting of the filter array on the forensic light source.
Figure 7:
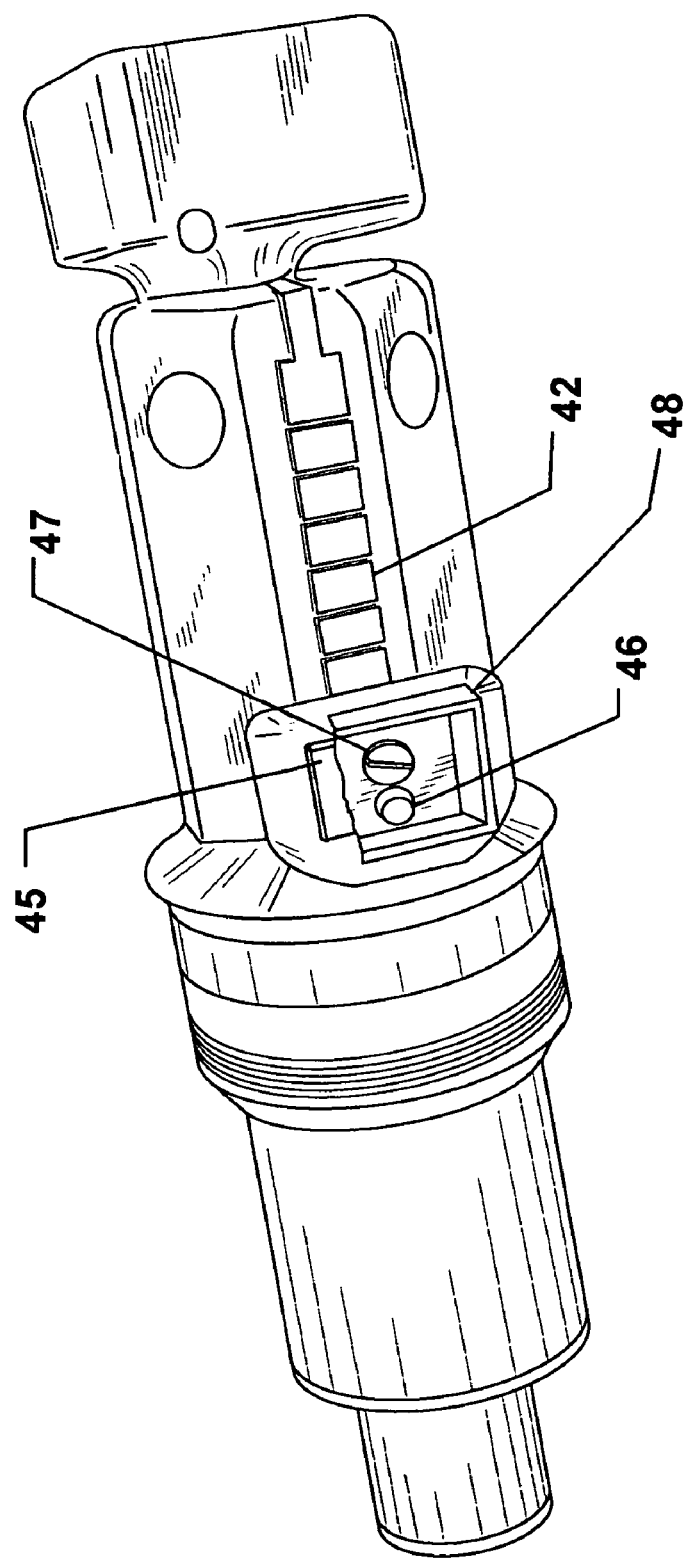
FIG. 7 is a bottom perspective view illustrating the mounting coupler for attaching the forensic light source to the tripod.

Referring to FIGS. 2 and 3, the light source 12 comprises a lamp housing 34, a reflector housing 36, a filter housing 38, and a lens housing 40. The lamp housing 34 is a unitary, thin wall molded plastic component of high impact, heat resistant plastic. The lamp housing 34 includes an upper handle bracket 41 and a lower handle bracket 42 (FIG. 7). An on/off button switch 43 is disposed at the front of the bracket 41 for controlling illumination of the light source. A carrying handle 44 is slidably detachably carried on one of the brackets and lockable at selected longitudinal positions therealong. A battery pack 46, comprising the power unit for the source, is removably carried on the rear of the housing. A rechargeable 14.4 VDC NiCad battery is preferred. The housing 34 is manufactured to accept the light source and other components as described below. Referring to FIG. 7, an adapter plate 45 is attached to the base of the lamp housing 34 adjacent the front end of the lower handle bracket. The plate 45 is provided with a base hole for receiving the locating pin 46 and a threaded hole for receiving the attaching screw 47 of a conventional tripod mounting bracket 48, thereby facilitating ready mounting of the light source 12 on the tripod 14.

Figure 8:
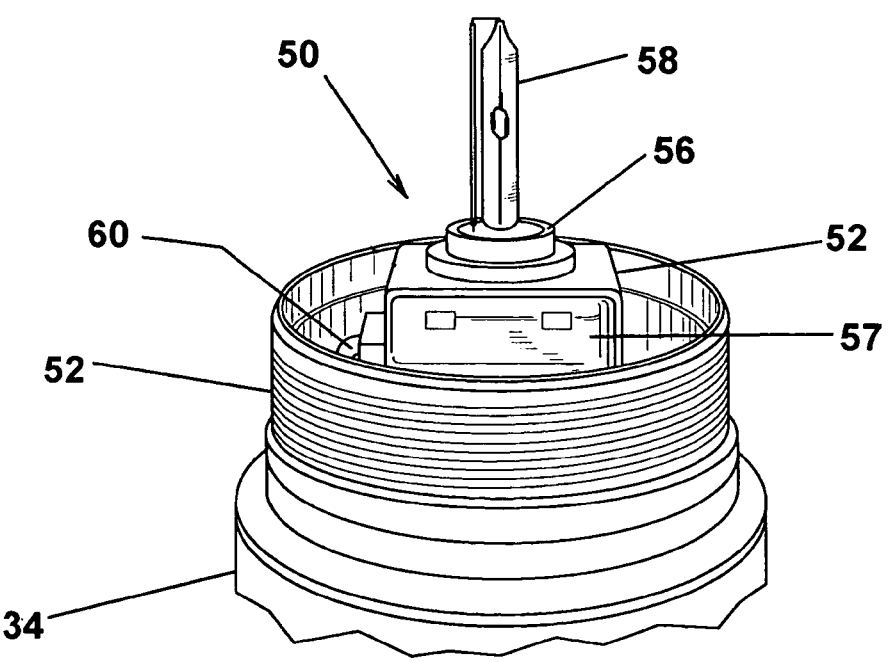
FIG. 8 is a fragmentary perspective view illustrating the mounting of the lamp unit.
Figure 11:
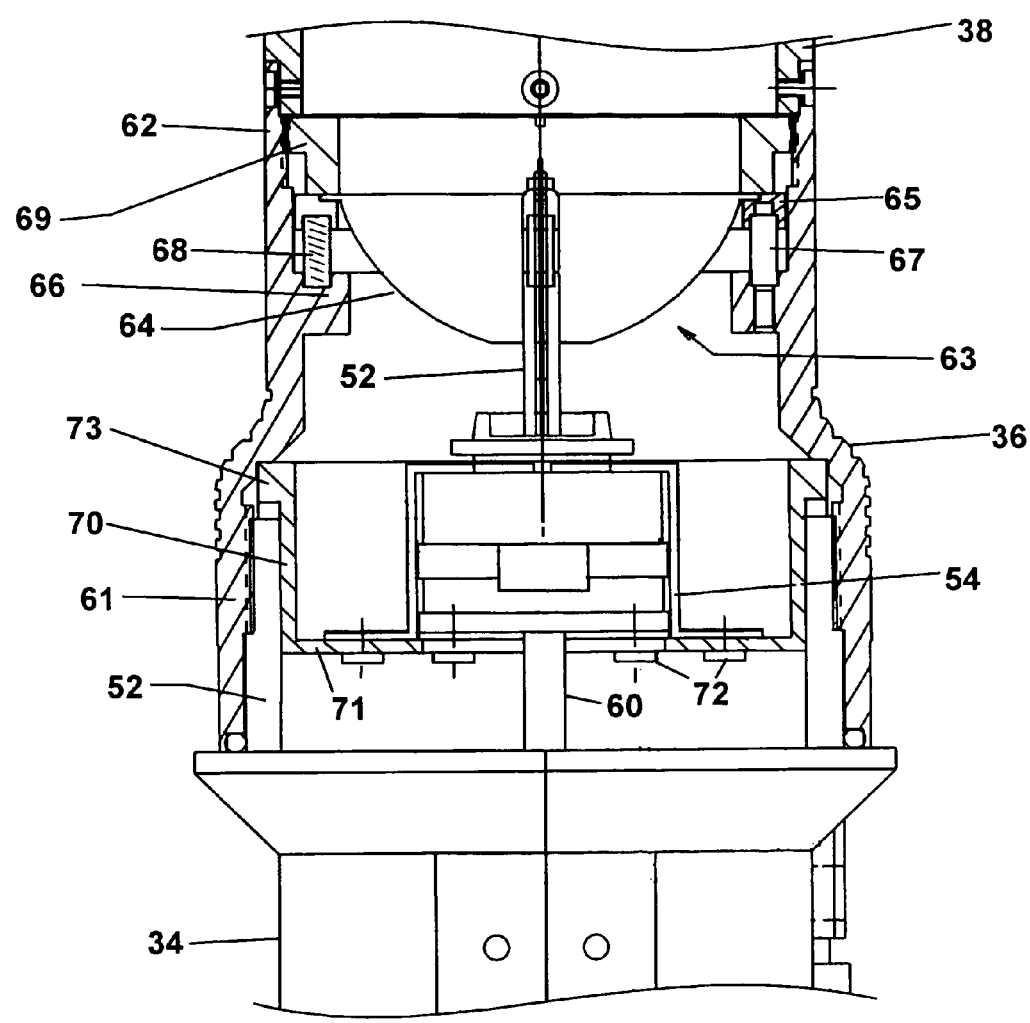
FIG. 11 is a fragmentary cross sectional view of the lamp unit and reflector housing.

As shown in FIGS. 8 and 11, a lamp assembly 50 is mounted in a molded collar 52 at the front of the lamp housing 34 by bracket 54. The light source 50 includes an igniter 56 and a high intensity xenon arc lamp 58. The igniter 56 includes a connector cable 60 extending rearwardly in the lamp housing 34 and connected with rearward exterior contacts that electrically engage mating contacts on a conventional electronic ballast, not shown.

A suitable lamp 58 is a Osram-Xenarc DIS high intensity xenon lamp/igniter, having a color temperature of around 4200° K, with a output of around 3200 lumens, and interfacing with the igniter 56 and connecting to a Gen4 removable ballast via the connector cable 60.

Referring to FIG. 2, fan units 63 are mounted interior of the lamp housing 34 adjacent a pair of screened ports 64 for removing the generated lamp heat during operation. Inlet air is drawn through a recess 90 (FIG. 12) beneath the filter slide 22 at the front of the unit for the purpose of maintaining low operating temperatures, at the filter slide, the lamp and throughout the entire unit during operation. Suitable fans are commercially available, with silent running, high volume fans preferred.

Referring to FIG. 11, the reflector housing 36 has a rear annular sleeve 61 that is threaded over the threaded collar of the lamp housing 34. The reflector housing 36 includes a front annular collar 62 having a counterbore within which a lamp assembly 63 including the lamp 52 is carried. The lamp assembly 63 further includes a parabolic polished reflector 64 having an annular frontal rim supported on a focus collar 65. The focus collar 65 is supported on an interior annular lip 66 in reflector housing 36 and axially guided by a plurality of guide pins 67 and biased upwardly by compression springs 68. An annular focus lock ring 69 is mounted in a threaded section of the reflector housing 36 above the focus collar 65. By appropriate rotation on the lock ring 69 the focus collar 65 and reflector 64 may be axially adjusted to focus the reflective surface with respect to the focal point of the lamp 52. The lamp 52 extends through a central aperture in the reflector 64 on the focal axis of the reflector. Accordingly, upon illumination, the emitted light is forwardly reflected as a focused circular beam.

The lamp assembly is mounted on a retainer ring 70 having an annular base 71 to which the legs of the mounting bracket 54 are attached by fasteners 72. The connector assembly for the lamp assembly extends rearwardly through a central opening in the base 71 into the housing 34. The retainer ring 70 includes an outer annular flange 73 retained in a rearwardly opening counterbore in the reflector housing and engaged by the sleeve 60 to fixedly mount the retainer ring and lamp 52.

Figure 12:
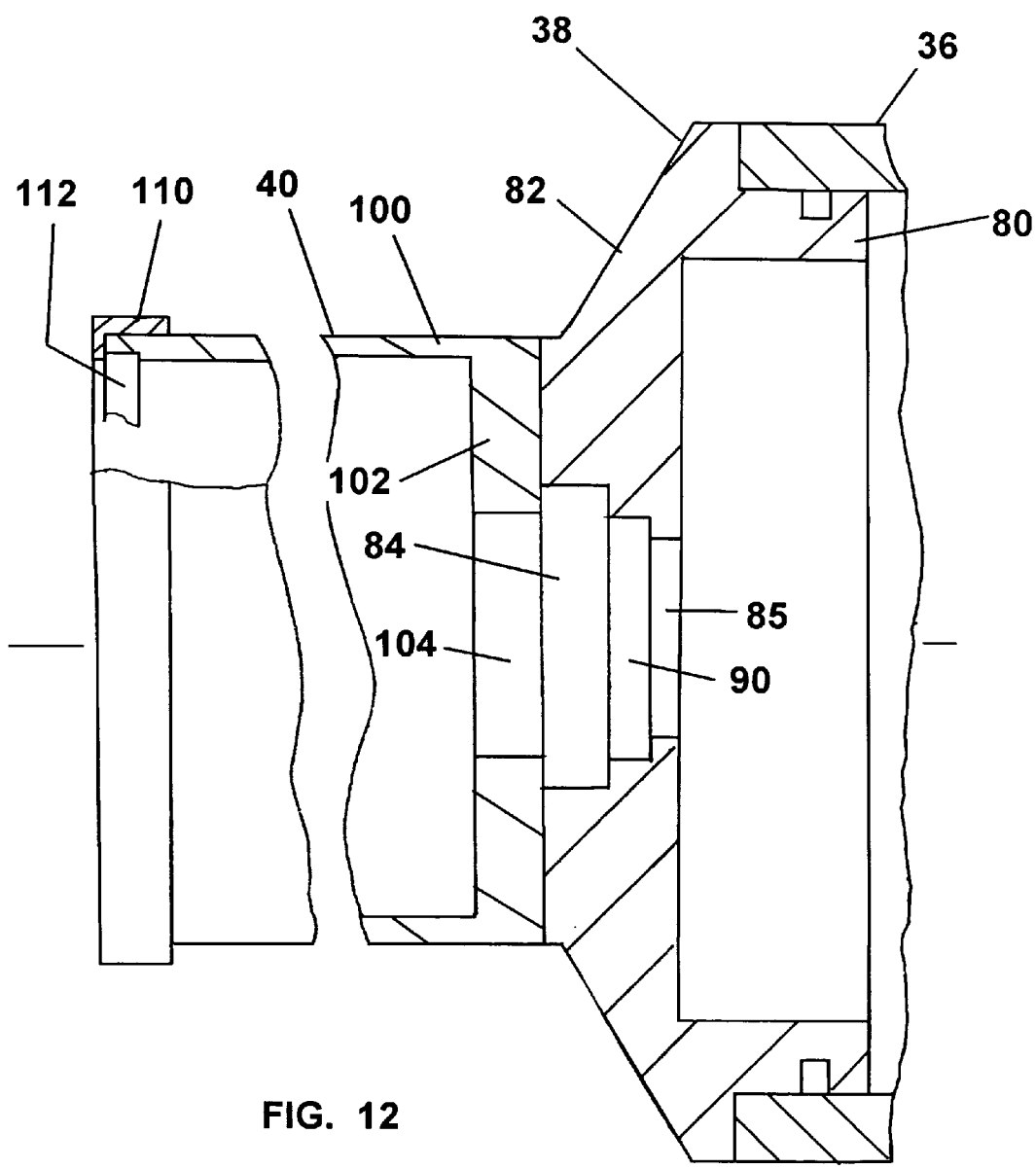
FIG. 12 is a fragmentary cross sectional view of the lens housing and the filter housing.

Referring to FIG. 12, the filter housing 38 includes an annular base 80 slidably received in the counterbore of the reflector housing 36 and secured thereto. The filter housing 38 includes a frontal conical flange 82 having a frontally opening transverse filter slot 84 and a central coaxial aperture 85. The lens housing 40 is connected to the front surface of the flange thereby establishing a transverse passage for slidably receiving a selected one of the filter slides 22. The air recess 90 is immediately behind the filter slot 84 and provides an air inlet for unit cooling as described above.

Figure 13:
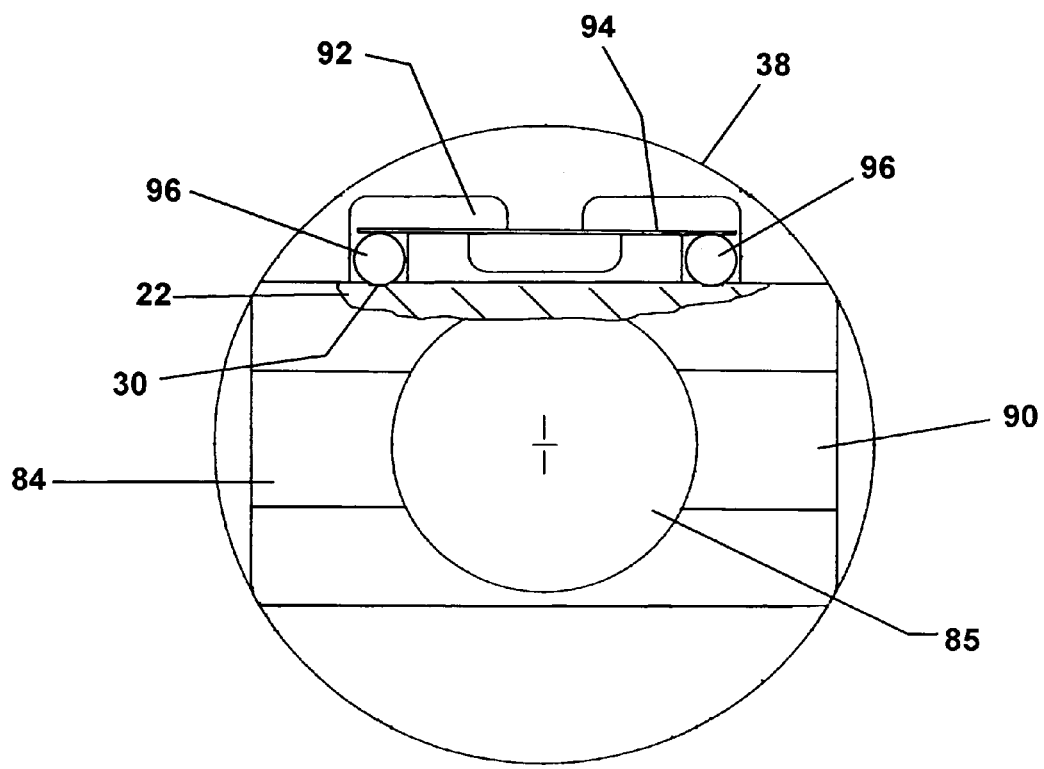
FIG. 13 is a front view of the filter housing illustrating the detenting of the filter slide.
Figure 14:
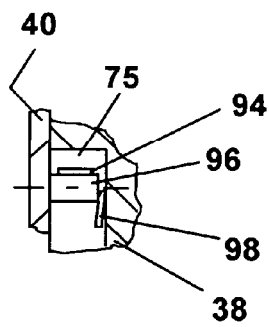
FIG. 14 is a fragmentary cross sectional view taken along line 15—15 in FIG. 14 illustrating the washer spring biasing the detent pin.

Referring to FIG. 13, the front face of the filter housing 38 includes a recessed M-shaped groove 92 having downwardly extending leg slots opening at the transverse filter slot 84. A leaf spring 94 is centrally retained between upper and lower ledges of the groove 92 with free ends registering with the legs. A pair of circular pins 96 are retained in the leg slots and biased downwardly by the free ends of the spring 94. As shown in FIG. 14, the pins 96 are upwardly biased by a concave circular shim spring 98, thereby limiting downward movement. When the slide is indexed in the slot, the pins are biased downwardly into the notches 30 to detent the slide with the filters coaxial with the aperture 69.

Referring to FIG. 12, the lens housing 40 includes a front cylindrical sleeve 100 and an annular base 102. The base 102 includes a central opening 104 coaxial with the opening 85 in the filter housing 38. The base 102 is secured to the flange 82 of the reflector housing 38 by fasteners, not shown. A cap assembly 110 including a focusing lens 112 is threadedly connected to the sleeve 100. Upon illumination of the lamp 52, the reflected illumination is projected through the openings and focused by the lens in a shallow angle circular beam.

The filter slides 22 are provided with excitation wavelength filters for use in detecting various forensic residues. Preferably, the kit 10 includes two filter slides, each carrying three differing filters and a single unfiltered opening. For optimum usage by the investigator, goggles having a barrier filter property are recommended for use with each filter; ultraviolet blocking, yellow, orange and red. Suitable such goggles are commercially available.

Unfiltered illumination is used for indoor and outdoor general crime scene search using the UV goggles. A 365 nm filter is used for detecting hair, fibers, and fluorescent materials using UV goggles. A 415 nm filter is used for detecting blood traces, semen, fluorescent materials using UV, yellow or orange goggles. A 450 nm filter is used for detecting semen on particular materials as well as fluorescent materials using as appropriate the yellow, orange or red goggles. A 470 nm filter is used for detecting DFO, fluorescent materials, and basic yellow dye stain using the yellow, orange or red goggles. A 505 nm filter is used for detecting DFO, cyanoacrylate prints stained with Rhodamine using orange or red goggles. A 530 nm filter is used for cyanoacrylate prints stained using the orange or red goggles. Generally, the orange goggles may be used with all visible light filters, i.e. the 415 nm to 530 filters, but due to the variations in excitation of certain materials, the investigator may employ the other colors for enhancing the detection. A label 90 is provided on the side of the lamp housing 30 listing the recommended goggles for use with each filter.

For general photography after detection, a lens barrier filter 28 is used on the recording camera in combination with the light source filter to best reveal the target material. Preferably, a plurality of lens barrier filters are provided, preferably orange, yellow and red.

It will thus be appreciated that the present invention provides a kit wherein all the equipment for investigation may be carried to a site and deployed for detecting and identifying forensic residue in a light weight unit free from connecting cables and battery packs. Appropriate filters may be accessed and readily installed to enable scanning of the site to a wide variety of evidence detectable only under discrete wavelengths. With the multiple handle positions, the unit with a single hand may be guided into confined spaces not accessible with prior units. After detection, the source may be fixedly mounted on the tripod to aid photographic recording of the identified residues.

Having thus described a presently preferred embodiment of the present invention, it will now be appreciated that the objects of the invention have been fully achieved, and it will be understood by those skilled in the art that many changes in construction and widely differing embodiments and applications of the invention will suggest themselves without departing from the sprit and scope of the present invention. The disclosures and description herein are intended to be illustrative and are not in any sense limiting of the invention, which is defined solely in accordance with the following claims.

What is claimed:

1. A light source for detecting forensic residues at a site that are not detectable under ambient lighting, said light source comprising: a thin walled housing member having an interior space including a frontal opening and a rear base; a rechargeable battery operatively removably mounted on said rear base; a handle member selectively removably attached to either a top surface or a bottom surface of said housing member; a source of white light mounted in said frontal opening; means including switch means carried on said housing member for electrically connecting said source to said battery; a reflector member surrounding said source for receiving illumination from said source and projecting reflected illumination forwardly; a cylindrical housing assembly including a frontal lens connected with said housing member at said frontal opening for receiving said reflected illumination from said reflector member and forwardly projecting illumination in a shallow angle beam; a transverse slot formed in said housing assembly and intersecting said reflected illumination; a first slide member slidable in said slot between a plurality of detented positions, said slide member having a first set of a plurality of wavelength filters for selectively illuminating certain of said forensic residues wherein one of said filters is interposed in said reflected illumination in one of said selected positions; an air inlet opening in said housing assembly immediately behind said slide member; an outlet opening in said housing member adjacent said base; and fan means in said housing member adjacent said outlet opening, said fan means being effective for drawing air through said inlet opening across said slide member and over said light source for maintaining cooling of said housing interior and said filters during operation.

2. The light source as recited in claim 1 including a second slide member having a second set of a plurality of wavelength filters for selectively illuminating other forensic residues.

3. The light source as recited in claim 2 wherein at least one of said slide members includes an unfiltered opening registering with said reflected illumination in one of said selected positions.

4. The light source as recited in claim 2 wherein said filters on one of said slide members have effective wavelength cutoffs of around 363 nm, 415 nm and 450 nm.

5. The light source as recited in claim 4 wherein said filters on the other of said slide members have effective wavelength cutoffs of around 470 nm, 505 nm, and 530 nm.

6. The light source as recited in claim 5 wherein said slide members include indicia identifying said wavelength cutoffs.

7. The light source as recited in claim 6 wherein each of said slide members has a plurality of spaced notches and detent means carried on said lens housing assembly selectively engage said notches to establish selectively said detented positions.

8. The light source as recited in claim 1 including a carrying case containing a second slide member, a tripod, coupling means on said housing member for attaching said light source to said tripod, a recharging assembly for said battery; a plurality of barrier filter goggles for wearing by said user during operation of said light source to enhance observing of said forensic residue; and a camera lens barrier filter for use on a camera for recording observed forensic residue.

9. The light source as recited in claim 8 wherein said barrier filter goggles have yellow, orange, red and UV clear coloration.

* * * * *